US012186413B2

(12) United States Patent
Nakashima et al.

(10) Patent No.: US 12,186,413 B2
(45) Date of Patent: Jan. 7, 2025

(54) NON-CELLULAR ROOT CANAL FILLER AND NON-CELLULAR DENTAL TISSUE REGENERATION PROMOTION KIT

(71) Applicant: KOWA COMPANY, LTD., Aichi (JP)

(72) Inventors: Misako Nakashima, Aichi (JP); Koichiro Iohara, Aichi (JP)

(73) Assignee: KOWA COMPANY, LTD., Aichi (JP)

( * ) Notice: Subject to any disclaimer, the term of this patent is extended or adjusted under 35 U.S.C. 154(b) by 619 days.

(21) Appl. No.: 17/441,611

(22) PCT Filed: Mar. 27, 2020

(86) PCT No.: PCT/JP2020/014166
§ 371 (c)(1),
(2) Date: Sep. 21, 2021

(87) PCT Pub. No.: WO2020/196867
PCT Pub. Date: Oct. 1, 2020

(65) Prior Publication Data
US 2022/0362109 A1    Nov. 17, 2022

(30) Foreign Application Priority Data
Mar. 28, 2019  (JP) ................. 2019-062054

(51) Int. Cl.
| *A61K 6/54* | (2020.01) |
| *A61K 6/69* | (2020.01) |
| *A61K 6/80* | (2020.01) |
| *A61K 31/4375* | (2006.01) |
| *A61K 31/4439* | (2006.01) |
| *A61K 31/451* | (2006.01) |
| *A61K 31/4725* | (2006.01) |
| *A61K 38/18* | (2006.01) |
| *A61K 38/19* | (2006.01) |
| *A61K 38/48* | (2006.01) |
| *A61K 45/06* | (2006.01) |
| *A61L 27/22* | (2006.01) |
| *A61L 27/36* | (2006.01) |
| *A61L 27/54* | (2006.01) |
| *A61P 1/02* | (2006.01) |

(52) U.S. Cl.
CPC ................. *A61K 6/54* (2020.01); *A61K 6/69* (2020.01); *A61K 6/80* (2020.01); *A61K 31/4375* (2013.01); *A61K 31/4439* (2013.01); *A61K 31/451* (2013.01); *A61K 31/4725* (2013.01); *A61K 38/1825* (2013.01); *A61K 38/193* (2013.01); *A61K 38/195* (2013.01); *A61K 38/4826* (2013.01); *A61K 45/06* (2013.01); *A61L 27/22* (2013.01); *A61L 27/3633* (2013.01); *A61L 27/54* (2013.01); *A61P 1/02* (2018.01); *C12Y 304/21004* (2013.01); *A61L 2300/412* (2013.01); *A61L 2300/414* (2013.01); *A61L 2300/434* (2013.01); *A61L 2300/436* (2013.01); *A61L 2430/12* (2013.01)

(58) Field of Classification Search
CPC ........ A61K 6/54; A61K 6/69; A61K 31/4375; A61K 38/1825; A61K 38/193; A61K 38/4826; A61K 31/4439; A61K 31/451; A61K 31/4725; A61K 38/195; A61K 45/06; A61K 6/80; A61L 27/3633; A61L 27/54; A61L 27/22; A61L 2300/412; A61L 2300/414; A61L 2300/434; A61L 2300/436; A61L 2430/12; A61P 1/02; C12Y 304/21004
See application file for complete search history.

(56) References Cited

U.S. PATENT DOCUMENTS

| 2010/0120844 A1 | 5/2010 | Sato et al. |
| 2011/0020310 A1 | 1/2011 | Nakashima et al. |
| 2012/0164604 A1 | 6/2012 | Nakashima et al. |
| 2014/0099605 A1 | 4/2014 | Nakashima et al. |
| 2014/0322672 A1 | 10/2014 | Nakashima et al. |
| 2019/0282675 A1 | 9/2019 | Nakashima et al. |
| 2019/0365804 A1 | 12/2019 | Khoury et al. |
| 2020/0261321 A1 | 8/2020 | Nakashima et al. |

FOREIGN PATENT DOCUMENTS

| EP | 3446723 B1 * | 4/2023 | ........... A61K 31/196 |
| JP | 2009173571 A | 8/2009 | |
| JP | 2009191048 A | 8/2009 | |
| JP | 5621105 B2 | 10/2014 | |
| JP | 5748194 B2 | 5/2015 | |
| JP | 5939559 B2 | 5/2016 | |
| JP | 6031658 B2 | 11/2016 | |

(Continued)

OTHER PUBLICATIONS

Iohara, Koichiro, et al., "Development of a Method for Promoting Dental Pulp Regeneration Using Trypsin in Elderly Dogs", The Congress of the Japanese Society for Regenerative Medicine, vol. 17, 2018 (2 pages, including machine English translation).

(Continued)

*Primary Examiner* — Patrick D Niland
(74) *Attorney, Agent, or Firm* — Myers Bigel, P.A.

(57) ABSTRACT

A non-cellular root canal filler comprises a tetrahydroisoquinoline compound or a pharmaceutically acceptable salt thereof, or a solvate of the compound or the salt, and a dental tissue regeneration promotion kit comprises a pretreatment agent comprising a serine protease, and the non-cellular root canal filler.

12 Claims, 7 Drawing Sheets

(56) References Cited

FOREIGN PATENT DOCUMENTS

| KR | 20150031210 A | 3/2015 |
|---|---|---|
| WO | 2008123582 A1 | 10/2008 |
| WO | 2017170996 A1 | 10/2017 |
| WO | 2018131003 A1 | 7/2018 |
| WO | 2019065478 A1 | 4/2019 |

OTHER PUBLICATIONS

First Chinese Office Action corresponding to CN 202080024967.7; dated Sep. 16, 2022 (9 pages, including English translation).
Extended European Search Report corresponding to EP Application No. 20776667.6, mailed Apr. 25, 2023 (6 pages).
International Search Report corresponding to PCT/JP2020/014166; dated Jun. 16, 2020 (3 pages, English translation only).
Cao, Y., et al., "Pulp-dentin Regeneration: Current State and Future Prospects", Journal of Dental Research 94(11), 2015, 1544-1551.
Del Fabbro, Massimo, et al., "Autologous Platelet Concentrates for Pulp and Dentin Regeneration: A Literature Review of Animal Studies", Journal of Endodontics 42(2), 2016, 250-257.
Galler, K. M., et al., "Clinical procedures for revitalization: current knowledge and considerations", International Endodontic Journal 49(10), 2016, 926-936.
He, Ling, et al., "Regenerative Endodontics for Adult Patients", Journal of Endodontics 43(9; Suppl.), 2017, S57-S64.
Iohara, Koichiro, et al., "A Novel Combinatorial Therapy With Pulp Stem Cells and Granulocyte Colony-Stimulating Factor for Total Pulp Regeneration", Stem Cells Translational Medicine 2(7), 2013, 521-533.
Kawamura, Rei, et al., "EDTA soluble chemical components and the conditioned medium from mobilized dental pulp stem cells contain an inductive microenvironment, promoting cell proliferation, migration, and odontoblastic differentiation", Stem Cell Research & Therapy 7(1; Article No. 77), 2016, 1-14.
Kontakiotis, Evangelos G., et al., "Regenerative Endodontic Therapy: A Data Analysis of Clinical Protocols", Journal of Endodontics 41(2), 2015, 146-154.
Nakashima, Misako, et al., "Pulp regeneration by transplantation of dental pulp stem cells in pulpitis: a pilot clinical study", Stem Cell Research & Therapy 8(Article No. 61), 2017, 1-13.
Noguchi, Yoshikuni, et al., "Clinical Studies on the Enzyme Tryspin, Especially on the Histochemical Significance of Enzymatic Debridement of the Necrotic Skin Lesion", The Japanese journal of dermatology and venereology: Official Organ of the Japanese Dermatological Association, 64(8); English abstract, 1954, 497-506.
Yang, Jingwen, et al., "Pulp Regeneration: Current Approaches and Future Challenges", Front. Physiol. 7(Article 58), 2016, 1-8.

* cited by examiner

COMPOUND B

SB328437

COMPOUND B

SB328437

COMPOUND B

SB328437

FIG.3A
TRYPSIN PRETREATMENT (+)
COMPOUND B (+)
G-CSF(+) 1M
FIG.3C
TRYPSIN PRETREATMENT (+)
COMPOUND B (-)
G-CSF(+) 1M
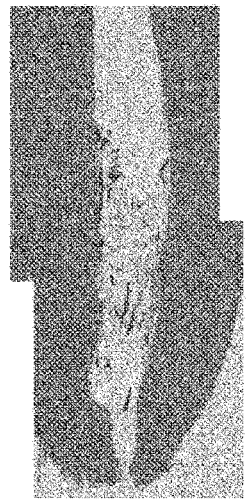
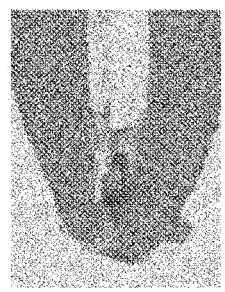
FIG.3B
FIG.3D
FIG.3E
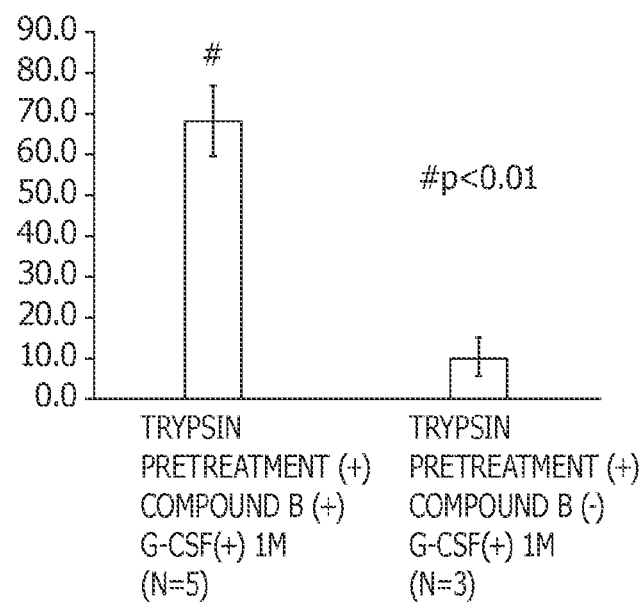

TRYPSIN PRETREATMENT (+)
COMPOUND B (+)
G-CSF(+) 1M

TRYPSIN PRETREATMENT (+)
COMPOUND B (-)
G-CSF(+) 1M

TRYPSIN PRETREATMENT (+)
COMPOUND B (+)
G-CSF(+) 1M

TRYPSIN PRETREATMENT (+)
COMPOUND B (-)
G-CSF(+) 1M

TRYPSIN PRETREATMENT (+)
COMPOUND B (+)
G-CSF(+) 1M

TRYPSIN PRETREATMENT (-)
COMPOUND B (+)
G-CSF(+) 1M

TRYPSIN PRETREATMENT (+)
COMPOUND B (+)
G-CSF(+) 1M

TRYPSIN PRETREATMENT (-)
COMPOUND B (+)
G-CSF(+) 1M

TRYPSIN PRETREATMENT (+)
COMPOUND B (+)
G-CSF(+) 1M

TRYPSIN PRETREATMENT (-)
COMPOUND B (+)
G-CSF(+) 1M

TRYPSIN PRETREATMENT (+)
COMPOUND C (+)
G-CSF(+) 1M

TRYPSIN PRETREATMENT (+)
COMPOUND C (-)
G-CSF(+) 1M

TRYPSIN PRETREATMENT (+) COMPOUND C (+) G-CSF(+) 1M (N=3)

TRYPSIN PRETREATMENT (+) COMPOUND C (-) G-CSF(+) 1M (N=3)

TRYPSIN PRETREATMENT (+) COMPOUND C (+) G-CSF(+) 1M (N=3)

TRYPSIN PRETREATMENT (+) COMPOUND C (-) G-CSF(+) 1M (N=3)

NON-CELLULAR ROOT CANAL FILLER AND NON-CELLULAR DENTAL TISSUE REGENERATION PROMOTION KIT

RELATED APPLICATIONS

This application is a 35 U.S.C. § 371 national phase entry of PCT Application PCT/JP2020/014166, filed Mar. 27, 2020, and published in Japanese on Oct. 1, 2020, as International Publication No. WO 2020/196867, and which claims the benefit of Japanese Application No. 2019-062054, filed Mar. 28, 2019, the disclosure of which is incorporated herein by reference in its entirety.

TECHNICAL FIELD

The present invention relates to a non-cellular root canal filler and to a non-cellular dental tissue regeneration promotion kit which promote the regeneration of dental pulp, dentin, and periapical tissues, without the use of stem cells or stem cell components.

BACKGROUND ART

Healthy teeth and the ability to chew well are important for healthy longevity in a super-aging society. However, over 20% of the middle-aged and the elderly have a disease (infected root canal) in which a tooth, in which nerves have already been removed (pulpectomy) is reinfected several decades later and filled with pus under the root. Approximately 25% of these cases are difficult to completely cure even after treatment. Such chronic infective lesions have great systemic influence on elderly people with compromised immune systems. Many of the elderly, being administered a therapeutic drug for osteoporosis, should not undergo tooth extraction. Even if tooth extraction is performed, the number of cases in which an implant can be used is decreased in the middle-aged and the elderly.

Meanwhile, tooth loss leads to impairment of occlusion, speech, taste, tactile sensation, or aesthetics, or reduction in QOL (quality of life). Recently, there have been concerns that oral frailty ascribable to a decline in tooth or oral function may lead to sarcopenia, such as low muscle strength or low body functions, or functional declines ascribable to undernutrition or the like, eventually making the middle-aged and the elderly in need of nursing care.

Accordingly, for the maintenance of tooth and oral functions, dental pulp regeneration therapy has been developed which involves autologously transplanting dental pulp stem cells separated from an unnecessary autologous tooth, or allogeneically transplanting dental pulp stem cells separated from an unnecessary tooth of others, to restore the tooth to its original state without leading to an infected root canal and tooth extraction after pulpectomy (Patent Documents 1 to 3). Although the dental pulp is regenerated by autologously or allogeneically transplanting not only dental pulp stem cells, but also other tissue stem cells derived from bone marrow or fat, such tissue stem cell transplantation is inferior in amount of regenerated dental pulp, amount of angiogenesis, and amount of regenerated nerves compared to dental pulp stem cell transplantation (Patent Document 4). Clinical studies have already confirmed that dental pulp regeneration therapy by autologous dental pulp stem cell transplantation is safe, suggesting it is effective (Non-Patent Document 1).

The dental pulp regeneration treatment includes the stem cell therapy as described above, as well as cell homing. For young human teeth with immature roots, a method of filling a blood clot in the root canal without using the use of dental pulp stem cells is commonly practiced (Non-Patent Document 2). An alternative method involves injecting PRP (platelet-rich plasma) instead of a blood clot (Non-Patent Document 3). However, such approaches reportedly regenerate only fibrous or bone-like tissues, rich mainly in blood vessels, whereas regeneration of dental pulp-specific tissues is rarely seen (Non-Patent Document 4). In animal experiments, cell homing methods have been developed which involve using a cell growth factor or a cytokine such as stromal cell-derived factor 1α (SDF1α), basic fibroblast growth factor (bFGF), platelet-derived growth factor (PDGF), stem cell factor (SCF), and granulocyte colony-stimulating factor (G-CSF) as a chemotactic factor without the use of stem cells (Non-Patent Document 5). However, it has been reported that such approaches fail to regenerate a sufficient amount of dental pulp and mostly regenerate relatively dense fibrous connective tissues with blood vessels while the entire root canal may be calcified (Non-Patent Documents 6 and 7). From these findings, stem cells are considered to be essential for dental pulp tissue regeneration, particularly in teeth with mature roots (Non-Patent Document 8).

However, autologous stem cell transplantation has disadvantages in that an unnecessary autologous tooth, such as a wisdom tooth, is necessary for using dental pulp stem cells; confirmation of safety of processed cell products is expensive; cells cannot be immediately supplied when required; and in the middle-aged and the elderly, traits of stem cells have changed, leading to decrease in the total number of dental pulp stem cells that can be separated, and the culturing thereof is time-consuming. In allogeneic transplantation, the cost for confirmation of safety after production and processing of cells is less, as compared with autologous transplantation, due to increase in the number of cell products per lot, whereas there remain unsolved issues such as the problem of a source of teeth with safety ensured, legal problems such as rights of, and rewards to, human donors of teeth, when human dental pulp stem cells are commercialized, and the problem of safety of immune responses in humans.

Accordingly, it is desired to develop a technique for promoting the regeneration of dental tissues, i.e., dental pulp, dentin, and periapical tissues, after pulpectomy or treatment of an infected root canal, without use of stem cells or stem cell-derived components. In addition, further studies on stem cell sources that promote the migration of host cells suggest that appropriate signaling factors can be selected for use in dental pulp regeneration. Specifically, it is desired to develop a dental pulp regeneration method in the future using an appropriate signaling factor that promotes the migration of host stem cells having angiogenic ability and the ability to differentiate into nerves, and suppresses the migration of cells having osteogenic and cementogenic capacities (Non-Patent Document 9).

In particular, the dental pulp regeneration in middle-aged and elderly individuals is delayed compared with that of young individuals. It has been confirmed by recent animal experiments using dogs that in dental pulp regeneration treatment by dental pulp stem cell transplantation in middle-aged and elderly individuals, the dental pulp regeneration is promoted by transplanting an anti-CCL11 neutralizing antibody/CCR3 antagonist or an ALK5 inhibitor with dental pulp stem cells. Also, the dental pulp regeneration was promoted by pretreating the root canals of teeth in middle-aged and elderly individuals with trypsin before transplantation of dental pulp stem cells (Patent Document 5). The anti-CCL11 neutralizing antibody or the CCR3 antagonist inhibits the binding of CCL11 to CCR3 and thereby blocks signal transduction. Growth differentiation factor 11 (GDF11) binds to transforming growth factor β (TGF-β) superfamily receptors ACVR1B (also called ALK4), TGFBR1 (also called ALK5) and ACVR1C (also called ALK7) and transduces signals via ALK4 and ALK5. The ALK5 inhibitor blocks the GDF11 signal transduction. It is considered that at the time of dental pulp regeneration, secreted factors from dental pulp stem cells accumulated in dentin are released from the dentin to promote dental pulp regeneration (Non-Patent Document 10). The addition of the CCR3 antagonist to culture supernatant containing secreted factors from senescent dental pulp stem cells in vitro significantly increased the neurite extension promoting effect and migration promoting effect of the culture supernatant. The addition of the ALK5 inhibitor thereto significantly increased the angiogenetic ability of the culture supernatant and its neurite extension promoting effect. These results have suggested that the dental pulp regeneration promoting effect of the CCR3 antagonist or the ALK5 inhibitor in middle-aged and elderly dogs is based on blood vessel induction promoting, neurite extension promoting, and migration promoting effects. However, the transplantation of dental pulp stem cells with the CCR3 antagonist or ALK5 inhibitor was not found to be effective for dental pulp regeneration in young dogs (Patent Document 5).

Trypsin is used as a medicament for the purpose of decomposing necrotic tissues, blood clots, or denatured proteins, thereby rendering a wound surface normal to facilitate the action of antibiotics (Non-Patent Document 11). The seeding of dental pulp stem cells onto dentin surfaces treated with trypsin in vitro increased the adhesion of the cells and exhibited enhancement in differentiation into odontoblasts. It has been suggested that the dental pulp regeneration promoting effect of trypsin pretreatment in middle-aged and elderly dogs is based on the inactivation of inhibitory factors accumulated in middle-aged or elderly dentin or the activation of differentiation enhancing factors by the cleavage of precursors, increase in adhesion of cells to the dentin, and enhancement in differentiation of dental pulp stem cells into odontoblasts. However, the trypsin pretreatment was not found to be effective for promoting dental pulp regeneration in young dogs (Patent Document 5). The dental pulp regeneration was rarely observed in trypsin pretreatment alone without the transplantation of dental pulp stem cells, or in mere use of the CCR3 antagonist or the ALK5 inhibitor without the transplantation of dental pulp stem cells (Patent Document 5).

CITATION LIST

Patent Documents

Patent Document 1: Japanese Patent No. 5621105
Patent Document 2: Japanese Patent No. 6031658
Patent Document 3: Japanese Patent No. 5748194
Patent Document 4: Japanese Patent No. 5939559
Patent Document 5: WO 2017/170996

Non-Patent Documents

Non-Patent Document 1: Nakashima M., Iohara K., Murakami M., Nakamura H., Sato Y., Ariji Y., Matsushita K.: Pulp regeneration by transplantation of dental pulp stem cells in pulpitis: A pilot clinical study. Stem Cell Res Therapy. 8 (1): 61, 2017

Non-Patent Document 2: Galler K M.: Clinical procedures for revitalization: current knowledge and considerations. Int Endod J. 2016 October; 49 (10): 926-36
Non-Patent Document 3: Kontakiotis E G, Filippatos C G, Tzanetakis G N, Agrafioti A.: Regenerative endodontic therapy: a data analysis of clinical protocols. J Endod. 41 (2): 146-54. 2015
Non-Patent Document 4: Del Fabbro M, Lolato A, Bucchi C, Taschieri S, Weinstein R L.: Autologous platelet concentrates for pulp and dentin regeneration: a literature review of animal studies. J Endod. 42 (2): 250-7, 2016
Non-Patent Document 5: Yang J., Yuan G., Chen Z.: Pulp Regeneration: Current Approaches and Future Challenges. Front Physiol.: 7: 58, 2016
Non-Patent Document 6: He L, Kim S G, Gong Q, Zhong J, Wang S, Zhou X, Ye L, Ling J, Mao J J.: Regenerative endodontics for adult patients. J Endod. 43 (9S): S57-S64, 2017
Non-Patent Document 7: Iohara K, Murakami M, Takeuchi N, Osako Y, Ito M, Ishizaka R, Utunomiya S, Nakamura H, Matsushita K, Nakashima M.: A novel combinatorial therapy with pulp stem cells and granulocyte colony-stimulating factor for total pulp regeneration. Stem Cells Transl. Med. 2 (7): 521-533, 2013
Non-Patent Document 8: Cao Y, Song M, Kim E, Shon W, Chugal N, Bogen G, Lin L, Kim R H, Park N H, Kang M K.: Pulp-dentin Regeneration: Current State and Future Prospects. J Dent Res. 94 (11): 1544-51, 2015
Non-Patent Document 9: Yang J, Yuan G, Chen Z.: Pulp Regeneration: Current Approaches and Future Challenges. Front Physiol. 7: 58, 2016. eCollection 2016
Non-Patent Document 10: Kawamura R, Hayashi Y, Murakami H, Nakashima M.: EDTA soluble chemical components and the conditioned medium from mobilized dental pulp stem cells contain an inductive microenvironment, promoting cell proliferation, migration and odontoblastic differentiation. Stem Cell Res. Ther. 7 (1): 77, 2016
Non-Patent Document 11: The Japanese journal of dermatology and venereology: official organ of the Japanese Dermatological Association, Vol. 64, Yoshikuni Noguchi, et al., p. 497-506, 1954

SUMMARY OF INVENTION

Technical Problem to be Solved

The present invention has been made in light of the problems described above. An object of the present invention is to provide a non-cellular root canal filler that is capable of effectively regenerating dental tissues without transplanting autologous or allogeneic stem cells or stem cell-derived components (extracellularly secreted proteins and exosome, etc.) in performing dental tissue regeneration. Another object of the present invention is to provide a non-cellular dental tissue regeneration promotion kit using the non-cellular root canal filler.

Solution to Problem

The present inventors have earnestly researched, and as a result, have found a tetrahydroisoquinoline compound that promotes dental tissue regeneration.

Specifically, according to one embodiment, the present invention provides a non-cellular root canal filler comprising a tetrahydroisoquinoline compound represented by the following formula (1):

[Formula 1]

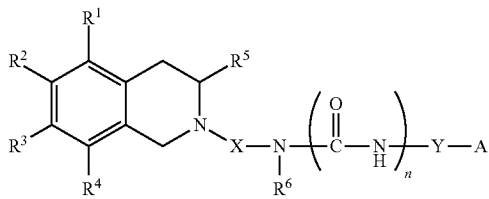

(1)

wherein $R^1$, $R^2$, $R^3$ and $R^4$ are each independently —H, -halogen, substituted or unsubstituted $C_{1-6}$ alkyl, —OH, —O—$C_{1-6}$ alkyl, —SH, —S—$C_{1-6}$ alkyl, —COOH, —CO—$C_{1-6}$ alkyl, —CO—O—$C_{1-6}$ alkyl, —CO—NH—$C_{1-6}$ alkyl, —NO$_2$, —NH$_2$, —NH—$C_{1-6}$ alkyl, —N($C_{1-6}$ alkyl)$_2$, or —NH—CO—$C_{1-6}$ alkyl, $R^5$ is substituted or unsubstituted $C_{1-6}$ alkyl, substituted or unsubstituted $C_{3-10}$ cycloalkyl, substituted or unsubstituted $C_{6-14}$ aryl, —$C_{1-6}$ alkylene-substituted or unsubstituted $C_{3-10}$ cycloalkyl, or —$C_{1-6}$ alkylene-substituted or unsubstituted $C_{6-14}$ aryl, $R^6$ is —H, substituted or unsubstituted —$C_{1-6}$ alkyl, or —Y'-A', X is $C_{1-6}$ alkylene, Y and Y' are each independently a single bond or $C_{1-6}$ alkylene, A and A' are each independently substituted or unsubstituted $C_{6-14}$ aryl or a substituted or unsubstituted 3- to 15-membered heterocyclic group, and n is 0 or 1;

or a pharmaceutically acceptable salt thereof or a solvate thereof.

The non-cellular root canal filler preferably comprises (+)-4-[[2-[6-fluoro-3-(4-fluorobenzyl)-3,4-dihydroisoquinolin-2(1H)-yl]ethylamino]methyl]-N-isopropylaniline monofumarate or (+)-N-[3-(methanesulfonylamino)benzyl]-2-[6-fluoro-3-(4-fluorobenzyl)-3,4-dihydroisoquinolin-2(1H)-yl]ethanamine monocitrate.

The non-cellular root canal filler may further comprise extracellular matrix.

The non-cellular root canal filler may further comprise an anti-CCL11 neutralizing antibody and/or an ALK5 inhibitor.

The non-cellular root canal filler may further comprise at least one chemotactic factor selected from the group consisting of G-CSF, bFGF and SDF-1.

The non-cellular root canal filler can be used in the dental tissue regeneration in a young individual or middle-aged and elderly individuals, preferably, a young individual.

According to one embodiment, the present invention also provides a dental tissue regeneration promotion kit comprising a pretreatment agent comprising a serine protease, and the non-cellular root canal filler.

The dental tissue regeneration promotion kit is preferably used in the dental tissue regeneration in middle-aged and elderly individuals.

The serine protease is preferably a chymotrypsin-like serine protease, more preferably trypsin.

Advantageous Effects of Invention

The non-cellular root canal filler and the dental tissue regeneration promotion kit according to the present invention are capable of effectively regenerating dental tissues without the need for transplanting autologous or allogeneic dental pulp stem cells or their stem cell-derived components, and are thus useful.

BRIEF DESCRIPTION OF DRAWINGS

FIG. 1 shows results of comparing a non-cellular dental pulp regeneration promotion kit using compound B with a non-cellular dental pulp regeneration promotion kit using SB 328437.

FIG. 2 shows results of comparing a non-cellular dental pulp regeneration promotion kit using compound B with a non-cellular dental pulp regeneration promotion kit using SB 328437.

FIG. 3 shows results of comparing a non-cellular dental pulp regeneration promotion kit using compound B with a non-cellular dental pulp regeneration promotion kit using no compound B. FIG. 3A is an image of HE staining of a dental tissue section treated with the non-cellular dental pulp regeneration promotion kit using compound B. FIG. 3B is an image (high resolution) of HE staining of the dental tissue section treated with the non-cellular dental pulp regeneration promotion kit using compound B. FIG. 3C is an image of HE staining of a dental tissue section treated with the non-cellular dental pulp regeneration promotion kit using no compound B. FIG. 3D is an image (high resolution) of HE staining of the dental tissue section treated with the non-cellular dental pulp regeneration promotion kit using no compound B. FIG. 3E is a graph showing results of quantitatively analyzing the amounts of the dental pulp regenerated by the non-cellular dental pulp regeneration promotion kit using compound B and the non-cellular dental pulp regeneration promotion kit using no compound B.

FIG. 4 shows results of comparing a non-cellular dental pulp regeneration promotion kit using compound B with a non-cellular dental pulp regeneration promotion kit using no compound B. FIG. 4C is an image of PGP9.5 immunostaining of a dental tissue section treated with the non-cellular dental pulp regeneration promotion kit using compound B.

FIG. 5 shows results of comparing the effect of a non-cellular root canal filler using compound B between with and without trypsin pretreatment.

FIG. 6 shows results of comparing the effect of a non-cellular root canal filler using compound B with and without trypsin pretreatment.

FIG. 7 shows results of comparing a non-cellular dental pulp regeneration promotion kit using compound C with a non-cellular dental pulp regeneration promotion kit using no compound C.

DESCRIPTION OF EMBODIMENTS

Figure 1A:
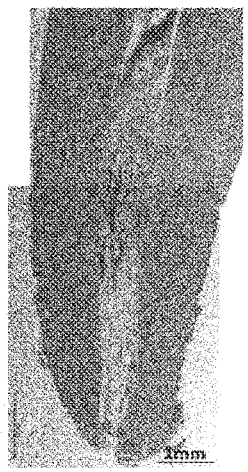
FIG. 1A is an image of HE staining of a dental tissue section treated with the non-cellular dental pulp regeneration promotion kit using compound B.

Hereinafter, the present invention will be described in detail. However, the present invention is not limited to the embodiments described in the present specification.

According to the first embodiment, the present invention provides a non-cellular root canal filler comprising a tetrahydroisoquinoline compound represented by the formula (1):

[Formula 2]

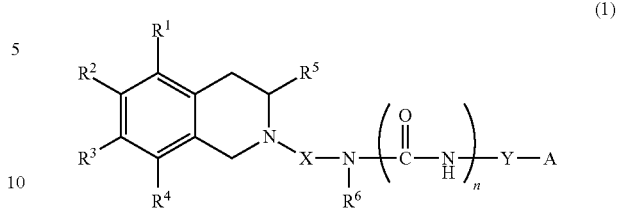

wherein $R^1$, $R^2$, $R^3$ and $R^4$ are each independently —H, -halogen, substituted or unsubstituted $C_{1-6}$ alkyl, —OH, —O—$C_{1-6}$ alkyl, —SH, —S—$C_{1-6}$ alkyl, —COOH, —CO—$C_{1-6}$ alkyl, —CO—O—$C_{1-6}$ alkyl, —CO—NH—$C_{1-6}$ alkyl, —NO$_2$, —NH$_2$, —NH—$C_{1-6}$ alkyl, —N($C_{1-6}$ alkyl)$_2$, or —NH—CO—$C_{1-6}$ alkyl, $R^5$ is substituted or unsubstituted $C_{1-6}$ alkyl, substituted or unsubstituted $C_{3-10}$ cycloalkyl, substituted or unsubstituted $C_{6-14}$ aryl, —$C_{1-6}$ alkylene-substituted or unsubstituted $C_{3-10}$ cycloalkyl, or —$C_{1-6}$ alkylene-substituted or unsubstituted $C_{6-14}$ aryl, $R^6$ is —H, substituted or unsubstituted —$C_{1-6}$ alkyl, or —Y'-A', X is $C_{1-6}$ alkylene, Y and Y' are each independently a single bond or $C_{1-6}$ alkylene, A and A' are each independently substituted or unsubstituted $C_{6-14}$ aryl or a substituted or unsubstituted 3- to 15-membered heterocyclic group, and n is 0 or 1;

or a pharmaceutically acceptable salt thereof or a solvate thereof (hereinafter, referred to as "compound group A" in the present specification).

The term "non-cellular" means that cells or cell-derived components (e.g., extracellularly secreted proteins and the exosome) are not involved. The term "root canal" refers to a canal in which the dental pulp is housed in the root portion of the tooth.

The non-cellular root canal filler of the present embodiment can comprise one compound alone or a mixture of two or more compounds selected from compound group A as an active ingredient. The compound of compound group A is a CCR3 antagonist which has an effect of inhibiting the binding of CCL11 to CCR3 by binding to the CCR3, and can suppress the signal transduction of CCL11.

The compound of compound group A used in the present embodiment is preferably N-[3-(methanesulfonylamino) benzyl]-2-[6-fluoro-3-(4-fluorobenzyl)-3,4-dihydroisoquinolin-2(1H)-yl]ethanamine (Example 126 of WO2008/123582; the following formula (2)); 4-[[2-[6-fluoro-3-(4-fluorobenzyl)-3,4-dihydroisoquinolin-2(1H)-yl]ethylamino]methyl]-N-isopropylaniline (Example 138 of WO2008/123582; the following formula (3)); 4-[[2-[6-fluoro-3-(4-fluorobenzyl)-3,4-dihydroisoquinolin-2(1H)-yl]ethylamino]methyl]-N-(2-methoxyethyl)aniline (Example 150 of WO2008/123582; the following formula (4)); or N-(pyridin-4-yl)methyl-2-[6-fluoro-3-(4-fluorobenzyl)-3,4-dihydroisoquinolin-2(1H)-yl]ethanamine (Example 180 of WO2008/123582; the following formula (5)) or a pharmaceutically acceptable salt thereof.

[Formula 3]

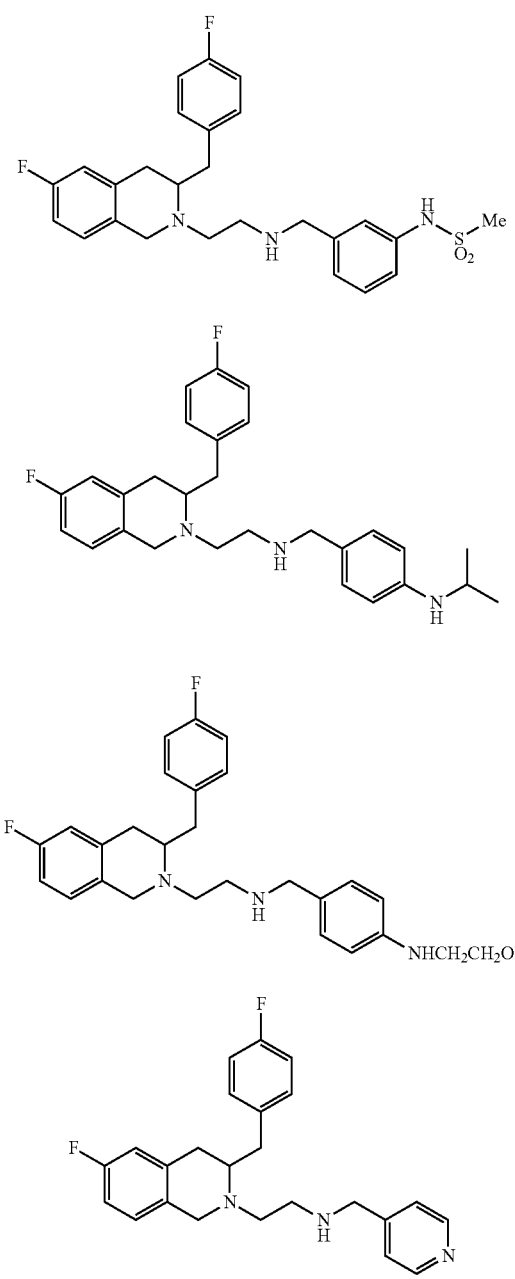

The compound of compound group A used in the present embodiment is particularly preferably (+)-4-[[2-[6-fluoro-3-(4-fluorobenzyl)-3,4-dihydroisoquinolin-2(1H)-yl]ethylamino]methyl]-N-isopropylaniline monofumarate (disclosed in JP 2009-173571 A, fumarate of the formula (3); also referred to as "compound B" in the present specification) or (+)-N-[3-(methanesulfonylamino)benzyl]-2-[6-fluoro-3-(4-fluorobenzyl)-3,4-dihydroisoquinolin-2(1H)-yl]ethanamine monocitrate (disclosed in JP 2009-191048 A, citrate of the formula (2); also referred to as "compound C" in the present specification).

The compound of compound group A can be produced by appropriately combining a chemical synthesis method described in WO2008/123582 and a chemical synthesis method equivalent thereto with various conventional methods known in the art.

The non-cellular root canal filler of the present embodiment may consist of only the active ingredient and may further comprise extracellular matrix, an anti-CCL11 neutralizing antibody and/or an ALK5 inhibitor, and/or at least one chemotactic factor selected from the group consisting of G-CSF, bFGF and SDF-1 as an optional component.

Examples of the extracellular matrix that can be used in the non-cellular root canal filler of the present embodiment include, but are not particularly limited to, collagen, artificial proteoglycan, gelatin, hydrogel, fibrin, phosphophoryn, heparan sulfate, heparin, laminin, fibronectin, alginic acid, hyaluronic acid, chitin, chitosan, PLA, PLGA, PEG, PGA, PDLLA, PCL, hydroxyapatite, β-TCP, and calcium carbonate. Alternatively, the extracellular matrix may be used in the form of coating on a metal substrate such as gold or titanium.

The anti-CCL11 neutralizing antibody that can be used in the non-cellular root canal filler of the present embodiment can be any antibody known in the art. The anti-CCL11 neutralizing antibody has an effect of inhibiting the binding of CCL11 to CCR3 by binding to the CCL11, and can suppress the signal transduction of CCL11. The anti-CCL11 neutralizing antibody is commercially available, and such a commercially available product can be used in the present embodiment.

The ALK5 inhibitor that can be used in the non-cellular root canal filler of the present embodiment can be any compound known in the art which inhibits GDF11 signal transduction. Various ALK5 inhibitors are commercially available, and such a commercially available product can be used in the present embodiment. Examples of the ALK5 inhibitor according to the present embodiment include, but are not limited to, any of the following compounds.

[Formula 4]

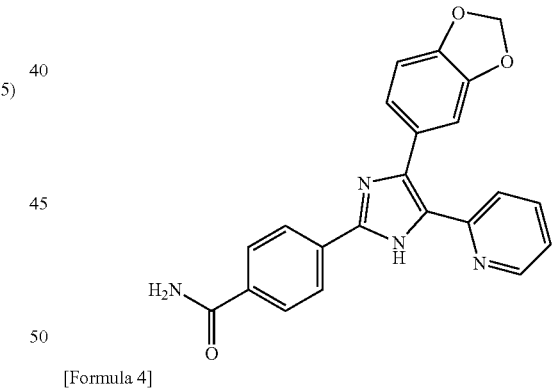

[Formula 4]

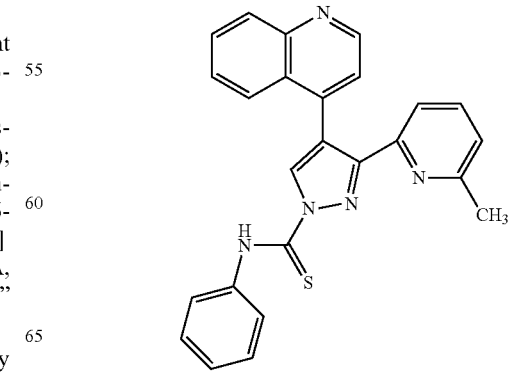

[Formula 4]

-continued

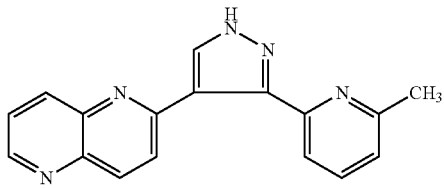

Examples of the chemotactic factor that can be used in the non-cellular root canal filler of the present embodiment include, but are not particularly limited to, G-CSF, SDF-1, bFGF, TGF-β, NGF, PDGF, BDNF, GDNF, EGF, VEGF, SCF, MMP3, Slit, GM-CSF, LIF, and HGF. One chemotactic factor alone, or a combination of two or more chemotactic factors selected therefrom, can be used. The chemotactic factor can promote the chemotactic activity of stem cells surrounding dental tissues. The chemotactic factor that can be used in the present embodiment is preferably selected from the group consisting of G-CSF, bFGF and SDF-1. All of these chemotactic factors are commercially available, and such a commercially available product can be used in the present embodiment.

In the non-cellular root canal filler of the present embodiment, the content of each of the components can fall within the range of, for example, 50 ng/ml to 200 μg/ml, and is preferably 3 μg/ml to 100 μg/ml. The mixing ratio between the active ingredient (compound of compound group A) and additional optional components is not particularly limited and may be, for example, 10% by weight: 90% by weight, to 90% by weight: 10% by weight. The non-cellular root canal filler of the present embodiment may be prepared from the components appropriately combined with a pharmaceutically acceptable diluent, carrier, excipient, or the like known in the art, as necessary.

The non-cellular root canal filler of the present embodiment is applicable both to young individuals and to middle-aged and elderly individuals and is preferably used in a young individual. In this context, the young individual is not particularly limited, and is, for example, a human 1 year of age or older and 29 years of age or younger, a rat at 1 week or more and 29 weeks or less after birth, or a dog at 1 week or more and 1 year or less after birth.

The non-cellular root canal filler of the present embodiment can be used by injection into the root canal, as in conventional dental root canal fillers known in the art.

According to the second embodiment, the present invention provides a dental tissue regeneration promotion kit comprising a pretreatment agent comprising a serine protease, and the non-cellular root canal filler.

The term "dental tissue" in the present embodiment means a tissue that encompasses at least one of dental pulp, dentin, and periapical tissues.

The "pretreatment agent" according to the present embodiment is used before insertion of the non-cellular root canal filler into the root canal. This can decompose a factor inhibiting tissue regeneration in dental tissues and periodontal tissues, and/or convert a latent form of a chemotactic factor or a differentiation enhancing factor to an active form.

The pretreatment agent used in the kit of the present embodiment comprises a serine protease. The serine protease is a protease (proteolytic enzyme) having a serine residue that performs nucleophilic attack as a catalytic residue. The serine protease is classified into subtilisin-like serine protease and chymotrypsin-like serine protease from similarity in amino acid sequence or conformation. The former includes subtilisin BPN', thermitase, proteinase K, lantibiotic peptidase, kexin, cucumisin, and the like, and the latter includes trypsin, chymotrypsin, thrombin, factor Xa, elastase, and the like. The serine protease that can be used in the present embodiment can be one enzyme alone, or a combination of two or more enzymes selected therefrom, and is preferably a chymotrypsin-like serine protease, more preferably trypsin.

The concentration of the serine protease in the pretreatment agent used in the kit of the present embodiment is not particularly limited as long as the serine protease at that concentration can decompose a factor inhibiting tissue regeneration in dental tissues and periodontal tissues, and/or convert a latent form of a chemotactic factor or a differentiation enhancing factor to an active form. The concentration can be, for example, 10 μg/ml (0.001%) to 50 mg/ml (5%), and it is preferably 500 μg/ml (0.05%) to 5 mg/ml (0.5%).

The pretreatment agent used in the present embodiment may further comprise nanobubbles. In this context, the "nanobubble" refers to an air bubble having a diameter in nanometers, or a lipid vesicle containing a gas or a gas precursor in its lumen and having a diameter in nanometers. The diameter of the nanobubble used in the pretreatment agent in the kit of the present embodiment is, for example, 10 to 500 nm, preferably 70 to 300 nm. The diameter of the nanobubble can be measured with, for example, a nanoparticle distribution measurement apparatus (SALD-7100, Shimadzu Corp.). The lipid composition, charged state, density, weight, etc. of the nanobubble can be appropriately determined. The lipid for use in the preparation of the nanobubbles is not particularly limited and can be, for example, phospholipid, glyceroglycolipid, and/or sphingoglycolipid or may be cationic lipid containing a primary amino group, a secondary amino group, a tertiary amino group or a quaternary ammonium group introduced in such lipid. The concentration of the nanobubbles in the pretreatment agent is not particularly limited and can be, for example, $2 \times 10^7$ nanobubbles/cm$^3$ to $2 \times 10^9$ nanobubbles/cm$^3$. The nanobubble concentration can be quantitatively analyzed by, for example, electron spin resonance (ESR).

The pretreatment can be performed by injecting the pretreatment agent into the root canal. The pretreatment time can be appropriately determined according to the type and concentration of the serine protease to be used. The pretreatment time can be, for example, 3 to 30 minutes, is preferably 5 to 20 minutes, and more preferably is 10 minutes.

The kit of the present embodiment may further comprise an additional buffer solution, reagent, instruction, and the like, in addition to the pretreatment agent and the non-cellular root canal filler.

The kit of the present embodiment is applicable both to young individuals and to middle-aged and elderly individuals, and is preferably used for middle-aged and elderly individuals. In this context, a middle-aged individual is not particularly limited and can be, for example, a human 30 years of age or older and 49 years of age or younger, a rat at 30 weeks or more and 39 weeks or less after birth, or a dog at 2 years or more and 4 years or less after birth. The elderly individual is not particularly limited and can be, for example, a human 50 years of age or older, a rat at 40 weeks or more after birth, or a dog at 5 years or more after birth. Thus, the kit of the present embodiment is preferably used in an individual which is a human 30 years of age or older, a rat at 30 weeks or more after birth, or a dog at 2 years or more after birth.

EXAMPLES

Hereinafter, the present invention will be further described with reference to Examples. However, the present invention is not by any means limited to these examples.

Example 1

Dental Pulp Regeneration after Pulpectomy in Young Dogs

After general anesthesia, pulpectomy was performed for maxillary and mandibular right and left anterior teeth in young (12-month-old) dogs. The openings were enlarged to the apex of the root with #55, then washed alternately with a 5% sodium hypochlorite solution and a 3% hydrogen peroxide solution, further washed with saline, dried, and then temporarily sealed with a resin completely. At 3 to 12 days after the pulpectomy, the temporary seals were removed, and the openings were washed alternately and washed with saline again. Then, the root canals were filled with 3% EDTA (Smear Clean, Nippon Shika Yakuhin Co., Ltd.), treated for 2 minutes, further washed with saline, and dried. Then, the root canals were pretreated by the application of trypsin preparation (5 mg of Francetin T powder (2,500 USP crystal trypsin per 10 mg, Mochida Pharmaceutical Co., Ltd.)/ml of 0.5% nanobubble water (prepared with Foamest 8 (NAC Corp.); see Koichiro Iohara and Misako Nakajima "Enhanced Delivery of Antibacterial Nanopolymers with Nanobubbles for the Complete Disinfection of the Root Canal System in a Canine Model of Intractable Periapical Disease", The Japanese Journal Of Conservative Dentistry, Vol. 63, No. 1, p. 73-82) for 10 minutes, and then washed with saline. Subsequently, a CCR3 antagonist (1.25 µg of compound B or 0.83 µg of SB328437 (Tocris Bioscience)) as a regeneration promoting compound and 150 ng of G-CSF (Neutrogin, Chugai Pharmaceutical Co., Ltd.) as a chemotactic factor were added to 20 µl of extracellular matrix collagen (Koken Atelocollagen Implant, Koken Co., Ltd.) to prepare a non-cellular root canal filler, which was then filled into the root canals. Then, a gelatin sponge for hemostasis (Spongel, Astellas Pharma Inc.) was placed thereon, and the cavities were completely sealed with glass ionomer cement and a photopolymerizable resin. Then, 28 days after transplantation, the teeth were extracted, and 5 µm paraffin sections were prepared on longitudinal sections according to a standard method, stained with H-E, and then morphologically observed. The amount of the regenerated dental pulp was evaluated by measuring the ratio of the area of regenerated dental pulp to the area of a dental pulp cavity as to four sections per sample, and calculating the mean of four samples. Angiogenesis was evaluated by staining day 28 specimens with Fluorescein labeled *Griffonia simplicifolia* (*Bandeiraea simplicifolia*) Lectin I (GSL I, BSL I) and Fluorescein labeled *Galanthus nivalis* (Snowdrop) Lectin (GNL) (Vector Laboratories) (20 µg/ml) for 15 minutes, followed by comparative examination. Neurite extension was evaluated by immunostaining day-28 specimens with an anti-PGP9.5 antibody (UltraClone, 1:10,000), followed by comparative examination.

Figure 1C:
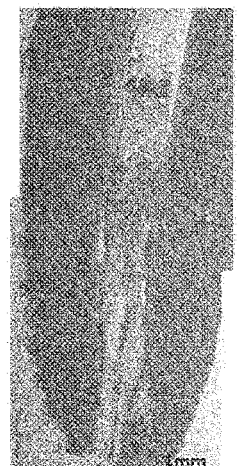
FIG. 1C is an image of HE staining of a dental tissue section treated with the non-cellular dental pulp regeneration promotion kit using SB 328437.
Figure 1B:
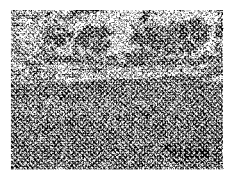
FIG. 1B is an image (high resolution) of HE staining of the dental tissue section treated with the non-cellular dental pulp regeneration promotion kit using compound B.
Figure 1D:
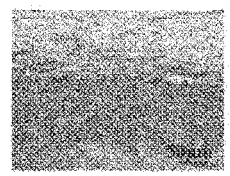
FIG. 1D is an image (high resolution) of HE staining of the dental tissue section treated with the non-cellular dental pulp regeneration promotion kit using SB 328437.
Figure 1E:
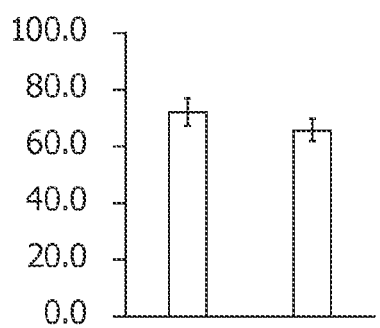
FIG. 1E is a graph showing results of quantitatively analyzing the amounts of the dental pulp regenerated by the non-cellular dental pulp regeneration promotion kit using compound B and the non-cellular dental pulp regeneration promotion kit using SB 328437.
Figure 2A:
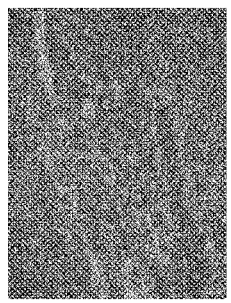
FIG. 2A is an image of lectin staining of a dental tissue section treated with the non-cellular dental pulp regeneration promotion kit using compound B.
Figure 2B:
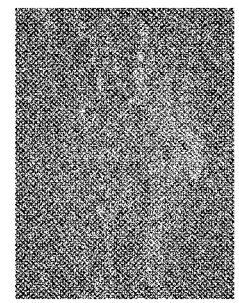
FIG. 2B is an image of lectin staining of a dental tissue section treated with the non-cellular dental pulp regeneration promotion kit using SB 328437.
Figure 2C:
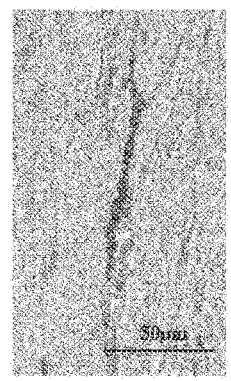
FIG. 2C is an image of PGP9.5 immunostaining of a dental tissue section treated with the non-cellular dental pulp regeneration promotion kit using compound B.
Figure 2D:
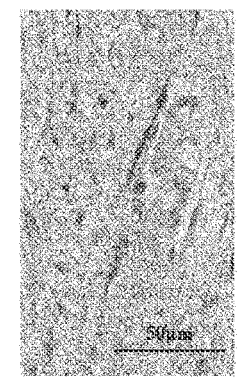
FIG. 2D is an image of PGP9.5 immunostaining of a dental tissue section treated with the non-cellular dental pulp regeneration promotion kit using SB 328437.

The results are shown in FIGS. 1 and 2. The non-cellular root canal fillers containing SB328437 or compound B as the CCR3 antagonist were found to cause dental pulp regeneration of loose connective tissues rich in blood vessels, whereas neither the infiltration nor internal absorption of inflammatory cells was observed (FIGS. 1A to 1D). The ratio of the regenerated dental pulp to a dental pulp cavity is shown in FIG. 1E. No statistically significant difference in the amount of the regenerated dental pulp was observed between the non-cellular root canal fillers containing SB328437 or compound B as the CCR3 antagonist (FIG. 1E). Angiogenesis (FIGS. 2A and 2B) and neurite extension (FIGS. 2C and 2D) were confirmed for both the non-cellular root canal fillers containing SB328437 or compound B as the CCR3 antagonist, demonstrating that odontoblast-like cells adhere to the side wall of the dentin to form dentin-like hard tissues.

Example 2

Comparison of Dental Pulp Regeneration after Pulpectomy in Young Dogs Between Presence and Absence of Compound B After general anesthesia, pulpectomy was performed for maxillary and mandibular right and left anterior teeth in young (11-month-old) dogs. The openings were enlarged to the apex of the root with #55, then washed alternately with a 5% sodium hypochlorite solution and a 3% hydrogen peroxide solution, and further washed with saline. The root canals were thoroughly dried with a paper point and temporarily sealed with cement and a resin completely after hemostasis. Then, 8 days after the pulpectomy, the temporary seals were removed, and the openings were washed alternately and washed with saline again. Then, the root canals were filled with 3% EDTA (Smear Clean, Nippon Shika Yakuhin Co., Ltd.), treated for 2 minutes, further washed with saline, and dried. Then, the root canals were pretreated by the application of a trypsin preparation (5 mg of Francetin T powder (2,500 USP crystal trypsin per 10 mg), Mochida Pharmaceutical Co., Ltd.)/ml of 0.5% nanobubble water (prepared with Foamest 8 (NAC Corp.); as described in Example 1)) for 10 minutes, and then washed with saline. Subsequently, 1.25 µg of compound B as a regeneration promoting compound and 150 ng of G-CSF (Neutrogin, Chugai Pharmaceutical Co., Ltd.) as a chemotactic factor were added to 20 µl of extracellular matrix collagen (Koken Atelocollagen Implant, Koken Co., Ltd.) to prepare a non-cellular root canal filler, which was then filled into the root canals. On the other hand, a non-cellular root canal filler having the same composition as above except for the absence of compound B was filled into the root canals by the same procedures as above and used as a control. Then, a gelatin sponge for hemostasis (Spongel, Astellas Pharma Inc.) was placed thereon, and the cavities were completely sealed with glass ionomer cement and a photopolymerizable resin. Then, 28 days after the transplantation, the teeth were extracted, and 5 µm paraffin sections were prepared on longitudinal sections according to a usual method, stained with H-E, and then morphologically observed in the same way as in Example 1. Angiogenesis and neurite extension were confirmed by BS-1 lectin staining and PGP9.5 immunostaining, respectively, in the same way as in Example 1.

Figure 4A:
FIG. 4A is an image of lectin staining of a dental tissue section treated with the non-cellular dental pulp regeneration promotion kit using compound B.
Figure 4B:
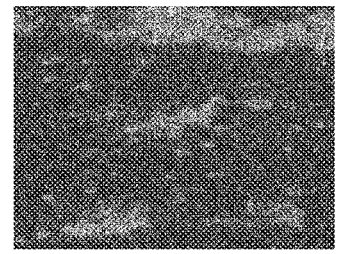
FIG. 4B is an image of lectin staining of a dental tissue section treated with the non-cellular dental pulp regeneration promotion kit using no compound B.
Figure 4C:
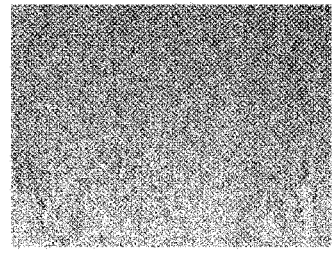
Figure 4D:
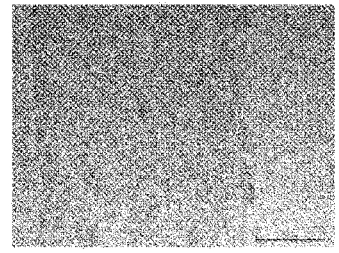
FIG. 4D is an image of PGP9.5 immunostaining of a dental tissue section treated with the non-cellular dental pulp regeneration promotion kit using no compound B.

The results are shown in FIGS. 3 and 4. Treatment with the non-cellular root canal filler containing compound B was found to sufficiently regenerate dental pulp-like tissues (FIGS. 3A and 3B), whereas treatment with the non-cellular root canal filler containing no compound B was found to regenerate such tissues only in a very small amount (FIGS. 3C and 3D). Statistically significant difference in the amount of the regenerated dental pulp was observed therebetween (FIG. 3E). On the other hand, similar angiogenesis (FIGS. 4A and 4B) and neurite extension (FIGS. 4C and 4D) were observed in both the cases. These results indicated that compound B is an effective component for the regeneration of dental pulp tissues.

Example 3

Comparison of Dental Pulp Regeneration after Pulpectomy in Young Dogs Between Presence and Absence of Trypsin Pretreatment After general anesthesia, pulpectomy was performed for maxillary and mandibular right and left anterior teeth in young (11-month-old) dogs. The openings were enlarged to the apex of the root with #50, then washed alternately with a 5% sodium hypochlorite solution and a 3% hydrogen peroxide solution, and further washed with saline. The root canals were thoroughly dried with a paper point and temporarily sealed with cement and a resin completely after hemostasis. After the pulpectomy, the temporary seals were removed, and the openings were washed alternately and washed with saline again. Then, the root canals were filled with 3% EDTA (Smear Clean, Nippon Shika Yakuhin Co., Ltd.), treated for 2 minutes, further washed with saline, and dried. Then, the left root canals were pretreated by the application of a trypsin preparation (5 mg of Francetin T powder (2,500 USP crystal trypsin per 10 mg), Mochida Pharmaceutical Co., Ltd.)/ml of 0.5% nanobubble water (prepared with Foamest 8 (NAC Corp.); as described in Example 1)) for 10 minutes, and then washed with saline. On the other hand, the right root canals were not subjected to the pretreatment (control). Subsequently, 1.25 µg of compound B as a regeneration promoting compound and 150 ng of G-CSF (Neutrogin, Chugai Pharmaceutical Co., Ltd.) as a chemotactic factor were added to 20 µl of extracellular matrix collagen (Koken Atelocollagen Implant, Koken Co., Ltd.) to prepare a non-cellular root canal filler, which was then filled into the right and left root canals. Then, a gelatin sponge for hemostasis (Spongel, Astellas Pharma Inc.) was placed thereon, and the cavities were completely sealed with glass ionomer cement and a photopolymerizable resin. Then, 28 days after the transplantation, the teeth were extracted, and 5 µm paraffin sections were prepared on longitudinal sections according to a usual method, stained with H-E, and were then morphologically observed in the same way as in Example 1. Angiogenesis and neurite extension were confirmed by BS-1 lectin staining and PGP9.5 immunostaining, respectively, in the same way as in Example 1.

Figure 5A:
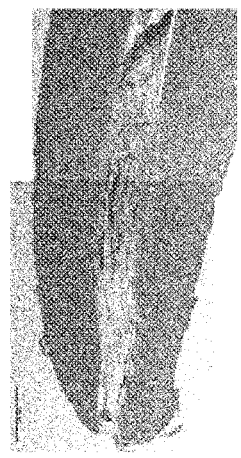
FIG. 5A is an image of HE staining of a dental tissue section with trypsin pretreatment.
Figure 5C:
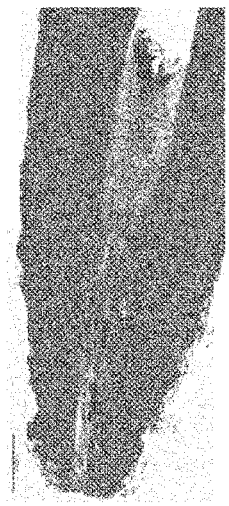
FIG. 5C is an image of HE staining of a dental tissue section without trypsin pretreatment.
Figure 5B:
FIG. 5B is an image (high resolution) of HE staining of the dental tissue section with trypsin pretreatment.
Figure 5D:
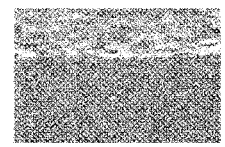
FIG. 5D is an image (high resolution) of HE staining of the dental tissue section without trypsin pretreatment.
Figure 5E:
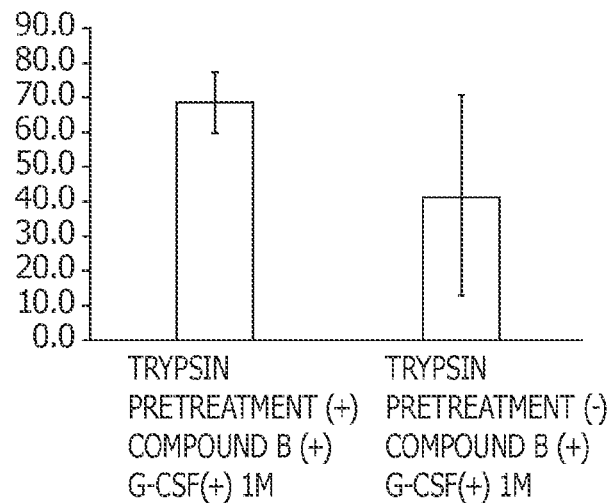
FIG. 5E is a graph showing results of quantitatively analyzing the amounts of the dental pulp regenerated by the non-cellular root canal filler using compound B between with and without trypsin pretreatment.
Figure 6A:
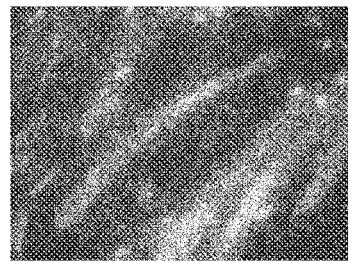
FIG. 6A is an image of lectin staining of a dental tissue section treated with a non-cellular dental pulp regeneration promotion kit with trypsin pretreatment.
Figure 6B:
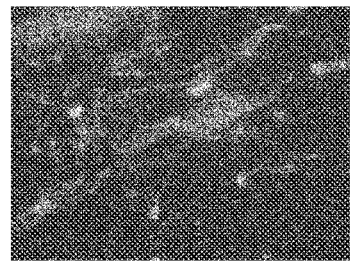
FIG. 6B is an image of lectin staining of a dental tissue section treated with the non-cellular dental pulp regeneration promotion kit without trypsin pretreatment.
Figure 6C:
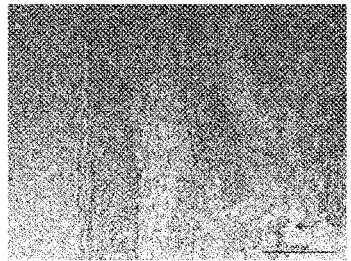
FIG. 6C is an image of PGP9.5 immunostaining of a dental tissue section with trypsin pretreatment.
Figure 6D:
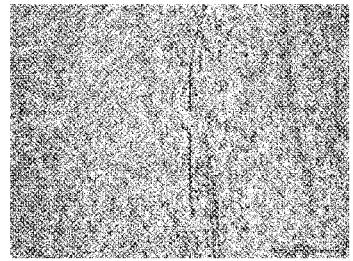
FIG. 6D is an image of PGP9.5 immunostaining of a dental tissue section without trypsin pretreatment.

The results are shown in FIGS. 5 and 6. The regeneration of dental pulp tissues was observed, regardless of whether trypsin pretreatment was performed or not (FIGS. 5A to 5D). The trypsin pretreatment performed tended to slightly increase the amount of regenerated dental pulp, albeit with no statistically significant difference (FIG. 5E). Also, the trypsin pretreatment performed tended to allow more odontoblast-like cells to adhere to the side wall of the dentin and form dentin-like hard tissues in a slightly higher amount (FIGS. 5A and 5B). Angiogenesis (FIGS. 6A and 6B) and neurite extension (FIGS. 6C and 6D) were similarly observed in both these cases. These results demonstrated that the injection of the non-cellular root canal filler without trypsin pretreatment regenerates the dental pulp with angiogenesis and neurite extension, and as in with trypsin pretreatment, allows odontoblast-like cells to adhere to the side wall of the dentin and promotes differentiation into odontoblasts and formation of dentin-like hard tissues.

Example 4

Comparison of Dental Pulp Regeneration after Pulpectomy in Young Dogs Between Presence and Absence of Compound C After general anesthesia, pulpectomy was performed for maxillary and mandibular right and left anterior teeth in young (11-month-old) dogs. The openings were enlarged to the apex of the root with #60, then washed alternatingly with a 5% sodium hypochlorite solution and a 3% hydrogen peroxide solution, and further washed with saline. The root canals were thoroughly dried with a paper point and temporarily sealed with cement and a resin completely after hemostasis. After the pulpectomy, the temporary seals were removed, and the openings were washed alternatingly and washed with saline again. Then, the root canals were filled with 3% EDTA (Smear Clean, Nippon Shika Yakuhin Co., Ltd.), treated for 2 minutes, further washed with saline, and dried. Then, the root canals were pretreated by the application of a trypsin preparation (5 mg of Francetin T powder (2,500 USP crystal trypsin per 10 mg), Mochida Pharmaceutical Co., Ltd.)/ml of 0.5% nanobubble water (prepared with Foamest 8 (NAC Corp.); as described in Example 1)) for 10 minutes, and was then washed with saline. Subsequently, 1.2 µg of compound C as a regeneration promoting compound and 150 ng of G-CSF (Neutrogin, Chugai Pharmaceutical Co., Ltd.) as a chemotactic factor were added to 20 µl of extracellular matrix collagen (Koken Atelocollagen Implant, Koken Co., Ltd.) to prepare a non-cellular root canal filler, which was then filled into the root canals. On the other hand, a non-cellular root canal filler having the same composition as above except for the absence of compound C was filled into the root canals by the same procedures as above and was used as a control. Then, a gelatin sponge for hemostasis (Spongel, Astellas Pharma Inc.) was placed thereon, and the cavities were completely sealed with glass ionomer cement and a photopolymerizable resin. Then, 28 days after the transplantation, the teeth were extracted, and 5 µm paraffin sections were prepared on longitudinal sections according to a usual method, stained with H-E, and then morphologically observed in the same way as in Example 1. The area of the dentin was evaluated by measuring the ratio of the area of the dentin to the area of a tooth as to one section per three samples, and calculating the mean of the three samples. The density of dentin cells was calculated by measuring the number of dentin cells included in the range of 1 mm from the side wall of the root canal as to one section per three samples.

Figure 7A:
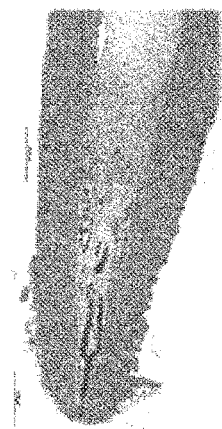
FIG. 7A is an image of HE staining of a dental tissue section treated with the non-cellular dental pulp regeneration promotion kit using compound C.
Figure 7B:
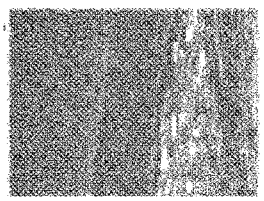
FIG. 7B is an image (high resolution) of HE staining of a dental tissue section treated with the non-cellular dental pulp regeneration promotion kit using compound C.
Figure 7C:
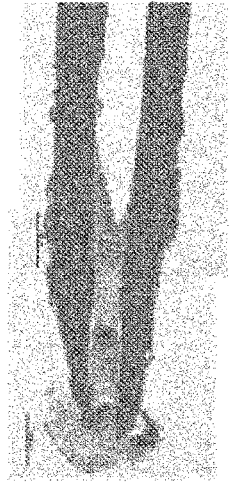
FIG. 7C is an image of HE staining of a dental tissue section treated with the non-cellular dental pulp regeneration promotion kit using no compound C.
Figure 7D:
FIG. 7D is an image (high resolution) of HE staining of a dental tissue section treated with the non-cellular dental pulp regeneration promotion kit using no compound C.
Figure 7E:
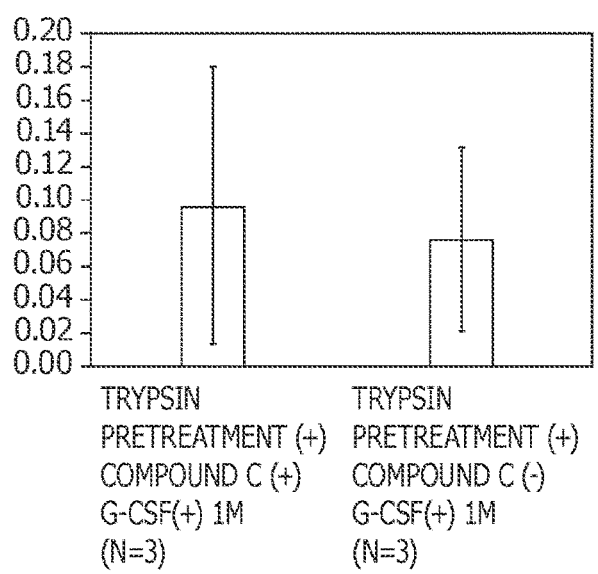
FIG. 7E is a graph showing results of quantitatively analyzing dental tissue regeneration by the non-cellular dental pulp regeneration promotion kit using compound C and the non-cellular dental pulp regeneration promotion kit using no compound C, on the basis of the area of the dentin.
Figure 7F:
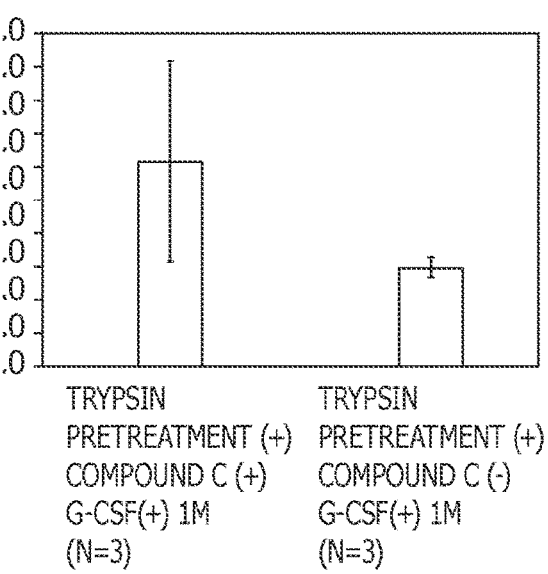
FIG. 7F is a graph showing results of quantitatively analyzing dental tissue regeneration by the non-cellular dental pulp regeneration promotion kit using compound C and the non-cellular dental pulp regeneration promotion kit using no compound C, on the basis of the density of odontoblasts.

The results are shown in FIG. 7. Treatment with the non-cellular root canal filler containing compound C was found to sufficiently regenerate dental pulp-like tissues (FIGS. 7A and 7B), whereas treatment with the non-cellular root canal filler containing no compound C was found to regenerate such tissues only in very small amounts (FIGS. 7C and 7D). The treatment with the non-cellular root canal filler containing compound C tended to increase the area of the dentin (FIG. 7E) and increased the density of dentin cells (FIG. 7F), as compared with the treatment with the non-cellular root canal filler containing no compound C. These results indicated that compound C is an effective component for the regeneration of dental pulp tissues.

The invention claimed is:

1. A non-cellular root canal filler comprising a tetrahydroisoquinoline compound, wherein the tetrahydroisoquinoline compound is selected from the group consisting of:
   (+)-4-[[2-[6-fluoro-3-(4-fluorobenzyl)-3,4-dihydroisoquinolin-2 (1H-yl]ethylamino]methyl]-N-isopropylaniline monofumarate; and
   (+)-N-[3-(methanesulfonylamino)benzyl]-2-[6-fluoro-3-(4-fluorobenzyl)-3,4-dihydroisoquinolin-2 (1H)-yl] ethanamine monocitrate.

2. The non-cellular root canal filler according to claim 1, further comprising extracellular matrix.

3. The non-cellular root canal filler according to claim 1, further comprising an anti-CCL11 neutralizing antibody and/or an ALK5 inhibitor.

4. The non-cellular root canal filler according to claim 1, further comprising at least one chemotactic factor selected from the group consisting of G-CSF, bFGF and SDF-1.

5. The non-cellular root canal filler according to claim 1 for use in the dental tissue regeneration in a young individual.

6. A dental tissue regeneration promotion kit comprising:
   a pretreatment agent comprising a serine protease; and
   a non-cellular root canal filler comprising a tetrahydroisoquinoline compound, wherein the tetrahydroisoquinoline compound is selected from the group consisting of:
   (+)-4-[[2-[6-fluoro-3-(4-fluorobenzyl)-3,4-dihydroisoquinolin-2 (1H)-yl]ethylamino]methyl]-N-isopropylaniline monofumarate; and
   (+)-N-[3-(methanesulfonylamino)benzyl]-2-[6-fluoro-3-(4-fluorobenzyl)-3,4-dihydroisoquinolin-2 (1H)-yl] ethanamine monocitrate.

7. The dental tissue regeneration promotion kit according to claim 6, wherein the non-cellular root canal filler further comprises extracellular matrix.

8. The dental tissue regeneration promotion kit according to claim 6, wherein the non-cellular root canal filler further comprises an anti-CCL11 neutralizing antibody and/or an ALK5 inhibitor.

9. The dental tissue regeneration promotion kit according to claim 6, wherein the non-cellular root canal filler further comprises at least one chemotactic factor selected from the group consisting of G-CSF, bFGF and SDF-1.

10. The dental tissue regeneration promotion kit according to claim 6, wherein the serine protease is a chymotrypsin-like serine protease.

11. The dental tissue regeneration promotion kit according to claim 10, wherein the chymotrypsin-like serine protease is trypsin.

12. The dental tissue regeneration promotion kit according to claim 6 for use in the dental tissue regeneration in middle-aged and elderly individuals.

* * * * *